(12) United States Patent
Sulatycke et al.

(10) Patent No.: US 9,536,277 B2
(45) Date of Patent: Jan. 3, 2017

(54) ASYNCHRONOUS METHOD AND APPARATUS TO SUPPORT REAL-TIME PROCESSING AND DATA MOVEMENT

(71) Applicant: Toshiba Medical Systems Corporation, Otawara-shi (JP)

(72) Inventors: Peter Daniel Sulatycke, Prospect Heights, IL (US); Hui Ning, Vernon Hills, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/532,804

(22) Filed: Nov. 4, 2014

(65) Prior Publication Data

US 2016/0125565 A1     May 5, 2016

(51) Int. Cl.
*G06T 1/20*     (2006.01)
*G09G 5/18*     (2006.01)
*G06F 19/00*    (2011.01)

(52) U.S. Cl.
CPC ............ *G06T 1/20* (2013.01); *G06F 19/3437* (2013.01); *G09G 5/18* (2013.01)

(58) Field of Classification Search
None
See application file for complete search history.

(56) References Cited

U.S. PATENT DOCUMENTS

| | | | | |
|---|---|---|---|---|
| 5,606,707 A * | 2/1997 | Tomassi | ............... | G06F 9/3877 345/418 |
| 6,470,071 B1 * | 10/2002 | Baertsch | .............. | A61B 6/4233 348/E5.086 |
| 8,311,791 B1 * | 11/2012 | Avisar | ................... | G09B 23/28 702/19 |
| 8,395,631 B1 * | 3/2013 | Wilt | ...................... | G06F 9/5016 345/502 |
| 2005/0219241 A1 * | 10/2005 | Chun | ................. | H04N 13/0493 345/419 |
| 2009/0276515 A1 * | 11/2009 | Thomas | ................. | A61B 19/56 709/223 |
| 2014/0204102 A1 * | 7/2014 | Rath | ........................ | G06T 1/20 345/522 |

* cited by examiner

*Primary Examiner* — Joni Richer
(74) *Attorney, Agent, or Firm* — Oblon, McClelland, Maier & Neustadt, L.L.P.

(57) ABSTRACT

An asynchronous medical image processing system is described that includes a real-time controller connectable to a medical imaging device, a graphics processing unit (GPU) connectable to a display device, and a central processing unit (CPU) that executes an operating system and related application(s). The real-time controller is directly connected to a memory of the GPU and performs respective operations asynchronously with respect to the CPU. The real-time controller additionally obtains medical imaging data, generates instructions for the medical imaging-data and transmits the medical imaging data and the instructions to the memory of the GPU. The GPU additionally receives and processes the medical imaging data based on the instructions from the real-time controller and instructions sent independently from the CPU.

18 Claims, 6 Drawing Sheets

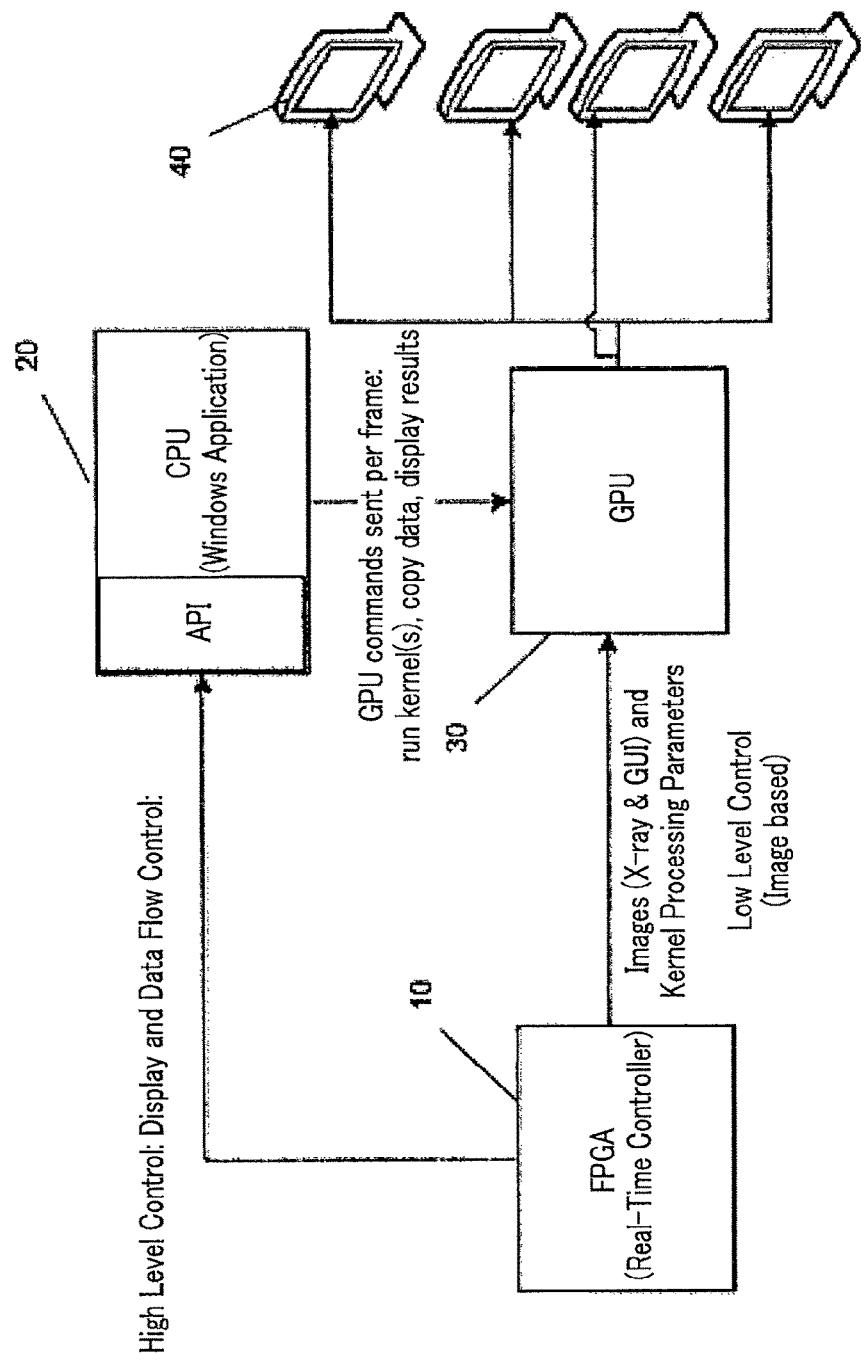
F I G. 1

ASYNCHRONOUS METHOD AND APPARATUS TO SUPPORT REAL-TIME PROCESSING AND DATA MOVEMENT

FIELD

Embodiments described herein relate generally to an asynchronous method and apparatus for supporting real-time processing and data movement in the display of images such as medical images.

BACKGROUND

In the field of real-time image display, there have been some attempts to devise systems that allow images to be directly injected (direct memory access (DMA) delivered) into a graphics card memory over Peripheral Component Interconnect Express (PCIe). However, no system is able to perform both display and real-time processing under the same operating system. For example, one system entitled "Sango" directly injects images into the graphic card's memory and allows an external PCIe card to trigger presentation of the next image within the graphics card based on the next Vsync signal. This allows images to be updated without involving the operating system (OS) of the host machine. Vsync stands for Vertical Synchronization and allows graphics processing units (GPUs) and display devices to synchronize the display of new images. The name originated from use of a vertical refresh of cathode-ray-tube-based displays.

In view of the above-described exemplary prior-art attempts, the field of real-time imaging still needs an improved method and device for tracking a probe position during examination sessions.

BRIEF DESCRIPTION OF THE DRAWINGS

A more complete appreciation of the embodiments described herein, and many of the attendant advantages thereof will be readily obtained as the same becomes better understood by reference to the following detailed description when considered in connection with the accompanying drawings, wherein:

FIG. 1 is a schematic diagram illustrating an embodiment of the medical image display apparatus;

DETAILED DESCRIPTION

Figure 2:
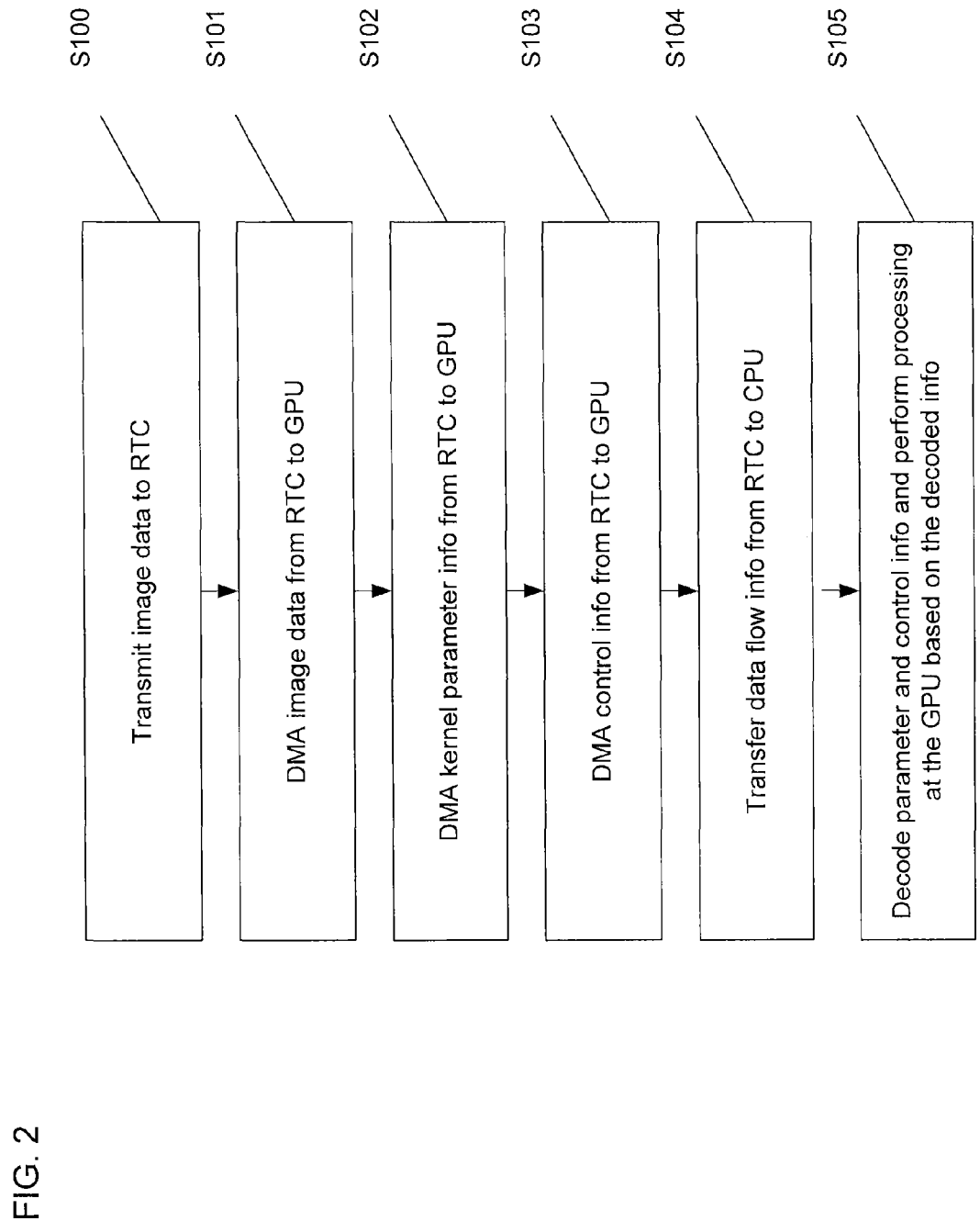
FIG. 2 is a flow diagram illustrating the process for performing asynchronous medical image processing according to one embodiment.

Real-time image display is necessary in many medical contexts. For instance, X-ray angiography requires that the system display real-time images with no glitches. In addition, because of compatibility issues it is often preferred that the user interface that displays the real-time images be one that operates on a commercially available operating system such as Windows™. However, it has been difficult in the past to display real-time images on a graphics card that is running on an OS such as Windows™ as Windows™ is not real-time. In particular, Windows™ often has large delays (glitches) that can cause the GPU to stall. If this happens during a medical procedure, the doctor will be seeing old images or no images, and this could harm the patient. In addition to displaying images in real-time, it is also highly beneficial for the graphics card to also perform real-time image processing. No known system can perform both display and real-time processing.

According to one embodiment there is described an asynchronous medical image processing system. The system includes a real-time controller connectable to a medical imaging device, a graphics processing unit (GPU) connectable to a display device, and a central processing unit (CPU) configured to execute an operating system and related application(s). The real-time controller is directly connected to a memory of the GPU and performs respective operations asynchronously with respect to the CPU. The real time controller is configured to obtain medical imaging data, generate instructions for the medical imaging-data and transmit the medical imaging data and the instructions to the memory of the GPU. The GPU is configured to receive and process the medical imaging data based on the instructions from the real-time controller and instructions sent independently from the CPU.

According to one embodiment there is described a real-time controller connectable to a medical imaging device. The real-time controller includes processing circuitry configured to obtain medical imaging data, generate instructions for the medical imaging data, and transmit the medical imaging data and the instructions to a memory of a graphic processing unit (GPU) connectable to a display device. The real-time controller is directly connected to a memory of the GPU and performs respective operations asynchronously with respect to a central processing unit configured to execute an operating system and related application(s).

According to one embodiment there is described a method for asynchronously processing medical images, using a medical image processing apparatus including a real-time controller connectable to a medical imaging device, a graphics processing unit (GPU) connectable to a display device, and a central processing unit (CPU) configured to execute an operating system and related application(s), the real-time controller being directly connected to a memory of the GPU and performing respective operations asynchronously with respect to the CPU. The method includes the steps of obtaining, at the real time controller, medical imaging data, generating, at the real time controller, instructions for the medical imaging-data, transmitting, from the real time controller, the medical imaging data and the instructions to the memory of the GPU, receiving the medical imaging data at the GPU, and processing, at the GPU, the medical imaging data based on the instructions from the real-time controller and instructions sent independently from the CPU.

Exemplary embodiments of medical display apparatus will be explained below in detail with reference to the accompanying drawings. Like reference numerals designate identical or corresponding parts throughout the several views. Now referring to FIG. 1, a schematic diagram illustrates an embodiment of a real-time image display system according to one embodiment.

The embodiment includes processing circuitry 10 which operates as a real-time controller. The real-time controller processing circuitry 10 can be implemented as a field-programmable gate array (FPGA), as an application-specific integrated chip (ASIC), a GPU, a PCI-based circuitry, or some other suitable device. The real-time controller processing circuitry 10 receives an input of imaging information from a medical imaging device, for example. This medical imaging device may be an X-ray angiography device, a CT device, an MRI device, a PET device, an ultrasound device, and/or any other newly emerging imaging diagnostic device, etc. The real-time controller processing circuitry 10 is connected to the GPU 30 and the CPU 20. The real-time controller processing circuitry 10 is connected to the GPU 30 via DMA and sends information directly into the memory of the GPU 30. The real-time controller processing circuitry 10 is connected to the CPU 20 via the operating system operating the CPU. In particular, the real-time controller processing circuitry 10 is connected to the CPU 20 via an application programming interface (API). The real-time controller processing circuitry 10, the CPU 20, and the GPU 30 all communicate asynchronously. The CPU 20 is also connected to the GPU 30 and sends commands for the processing and display of multiple (e.g. 16) future image frames to the GPU and CPU queues. The commands are first queued in a related CPU context queue and then fetched independently by the GPU 30 into its own queue. As result, if the CPU 20 stalls, the GPU 30 will continue running without a problem. With regard to the communication between the CPU 20 and GPU 30, this is performed independently of the real-time controller processing circuitry 10 such that CPU 20 and GPU 30 interact as if they do not realize that the real-time controller processing circuitry 10 even exists.

Asynchronous communication is needed to prevent any blockage between the real-time controller processing circuitry 10, the CPU 20, and GPU 30 that would cause delays in the system.

In order to accomplish asynchronous communication, the process illustrated in FIG. 2 is carried out. The steps may be performed in the order indicated in FIG. 2 or may performed in a different order. In one embodiment at least one of the steps may be conducted concurrently with another step.

In step 100, image data (for example, medical image data) is transmitted to the real-time controller processing circuitry 10 from an imaging device, such as, for example, a medical imaging device. The present implementation is not limited to medical imaging data, but may also be used for animation, image processing, or any other processing using a graphics processing unit.

In step 101, the image data is directly transferred by DMA to the GPU 30 from the real-time controller processing circuitry 10. The CPU 20 is not informed of the specific image data transferred to the GPU 30.

In step 102, kernel parameter information is directly transferred by DMA to the GPU 30 from the real-time controller processing circuitry 10. The kernel parameter information is information for controlling the GPU 30. Each kernel that runs on the GPU 30 takes different parameter inputs to control the processing on the GPU 30. For example, a transformation kernel requires an angle of rotation and shift value as input. Typically this data is generated and sent from an application that runs on the operating system of the CPU 20. However, in the present case, the kernel parameter information is received from the real-time controller processing circuitry 10. This is the case, at least, because it would be very inefficient to have the real-time controller processing circuitry 10 communicate the kernel parameter information to an application running on the operating system of the CPU 20, and then in turn, send this information to the GPU. More importantly this would introduce large latencies from when an image processing change is requested and when the processing occurs. Such latency would occur because the CPU 20 sends GPU 30 messages for future frames down to the GPU 30. Thus the GPU 30 would need to process all previous frames before it would receive the new processing instructions.

The same technique used for transmitting image data to the GPU 30 from the real-time controller processing circuitry 10 can be used to transfer kernel parameter information. All parameter information can be placed within a header that travels along with the image data. This means that all information to process an image is self-contained within the image transferred to the GPU 30 from the real-time controller processing circuitry 10. Alternatively, the parameter information could also be sent separately from the image data. The GPU 30 can decode the header and use the resulting information for the corresponding parameters.

Note that this eliminates any image frame latency from when real-time controller processing circuitry 10 indicates processing should change and when processing occurs. This same technique can be used to provide state information directly to pinned memory (such as PCIe addressable GPU 30 internal memory or GPU 30 addressable system memory), thereby allowing the GPU 30 to make decisions on what processing should actually occur. For example, the kernel could actually determine if the kernel should do its normal processing or just immediately return without executing the processing. This is all possible because decisions can be made inside of a kernel based on parameters sent into the kernel.

In step 103, control information is directly transferred by DMA to the GPU 30 from the real-time controller processing circuitry 10. The control information includes the frame or image number. The real-time controller processing circuitry 10 directly sends images to the GPU 30, and in turn the GPU 30 simply processes whatever image is present in its memory. Multiple buffers in pinned GPU memory can be used so that reading and writing can occur at the same time. The real-time controller processing circuitry 10 also generates an image number for each image that is transferred to the GPU 30 so that the GPU 30 can confirm which buffer is the most recent.

GPU-processed images will sometimes have to be sent back to real-time controller processing circuitry 10 for long-term storage and for sending to external PCs. In this circumstance, for example, real-time controller processing circuitry 10 will read images from the GPU 30 board pinned memory. To accomplish this, the real-time controller processing circuitry 10 will need to know when an image is completely processed. Note, even though many images will not need to be read back by the real-time controller processing circuitry 10, image completion information can be sent for all images to keep the design consistent and simple.

There are two exemplary ways of implementing this, on the first approach: the GPU 30 indicates that a new output image has been written to pinned memory by updating a register in the pinned memory indicating which buffer has most recently been updated. The real-time controller processing circuitry 10 polls this register at predetermined intervals (e.g. with every image write) and compares the value to a locally stored value in the real-time controller processing circuitry 10. The real-time controller processing circuitry 10 knows that one or more new output buffers have been written when the register value in the GPU 30 changes.

On the second approach, the GPU 30 writes the image number of the recently completed image directly to a memory location in real-time controller processing circuitry 10, via the GPU 30 DMA engine, indicating that an image is completely processed.

The first example provides some advantages, such as avoiding making use of the DMA engine. This will allow the solution to work on multiple types of commercially available GPU-based systems if access to pinned memory on the GPU is available. In addition, the first example makes communication between the GPU 30 and the real-time controller processing circuitry 10 consistent, which simplifies implementation and debug.

In step 104, only start/stop data flow information is transmitted from the real-time controller processing circuitry 10 to the CPU 20. During the processing of a dataflow, no additional communication between the real-time controller processing circuitry 10 and CPU 20 takes place except for the transmission of status information. The real-time controller processing circuitry 10 communicates with the CPU 20 when the processing of dataflow is to start or stop. The real-time controller processing circuitry 10 will also inform the CPU 20 which processing blocks should be performed for the dataflow that is starting up. The CPU 20 is not informed of what makes up a particular dataflow. The CPU 20 and GPU 30 are viewed as a service that is controlled by the real-time controller processing circuitry 10.

In step 105, the GPU 30 decodes the control and parameter information transmitted from the real-time controller processing circuitry 10 and makes decision(s) regarding what processing to perform within the GPU's kernels. This effectively removes the CPU 20 from the decision-making process regarding what processing should occur on any image, and ensures that all images are treated the same by the CPU 20. This allows the system to effectively bypass the operating system and enables substantial real-time capability. The GPU 30 then performs the processing on the image data.

The communication between the GPU 30 and the CPU 20 is designed to be asynchronous. However, there are many factors that can cause blocking and prevent asynchronous communication. Even when these two components are working asynchronously, there is a limit to their asynchronous nature because of the synchronization between the GPU 30 and the displays 40. In one example, a group of application programming interfaces, such as DirectX, provides a command, such as, for example, a MaxFrameLatency command, that allows the application to specify how many frames worth of messages can be queued ahead of time by the CPU 20 and the GPU 30. A frame is equivalent to the output image produced by GPU 30 instructions between application programming interface "present" commands. The "present" command is used to synchronize with the GPU 30 on Vsync. The CPU 20 will stop sending commands to the GPU 30 once the number of frames queued in the CPU 20 and the GPU 30 is equal to MaxFrameLatency.

The amount of queuing also depends on how fast the GPU 30 is processing images, and in turn, if the GPU 30 is blocking on Vsync with the displays 40. For example, if the GPU 30 does not take much time to process images, the GPU 30 will be throttled by Vsync and how many buffers are available for Vsync with the displays 40. In either case, to maximize the decoupling between the CPU 20 and the GPU 30, MaxFrameLatency should be set to the maximum allowable value (such as, for example, 16). This will minimize/eliminate how often the GPU 30 is blocked because of the CPU 20. More importantly, this will allow the GPU 30 to continue processing frames even when the CPU 20 may not be available. This is especially important in a non-real-time operating system where it is expected that the GPU 30 application and driver will be preempted by other processes. Typical delays under the operating system can be up to 30-50 ms. Buffering of up to 16 frames worth of commands allows the CPU 20 to stall for 267 ms (16/60 fps) without affecting the GPU 30 performance. This is exactly what is needed in a real-time system.

Assuming that the GPU 30 never stalls because of lack of input from the CPU 20, the number of frames displayed per second will depend on how long the computation of a frame takes and the maximum frame rate of the display. One example of a display used in an X-ray angiography system, for example, can update 60 frames per second. If the GPU 30 computation time is sufficiently small (fast computation), the maximum frame rate may be equal to the frame rate of the display. For instance, in the example of the display that updates at 60 frames per second, if the GPU 30 computation is any longer than 1/60 of a second, the frame rate displayed will be less than 60 fps. For example, if it takes 33 ms to process a frame, the displayed output will be 30 fps. Thus, the CPU 20 and GPU 30 communicate asynchronously, but communication can still be blocked if the GPU 30 is busy or if the GPU 30 is blocking due to the display.

Figure 3:
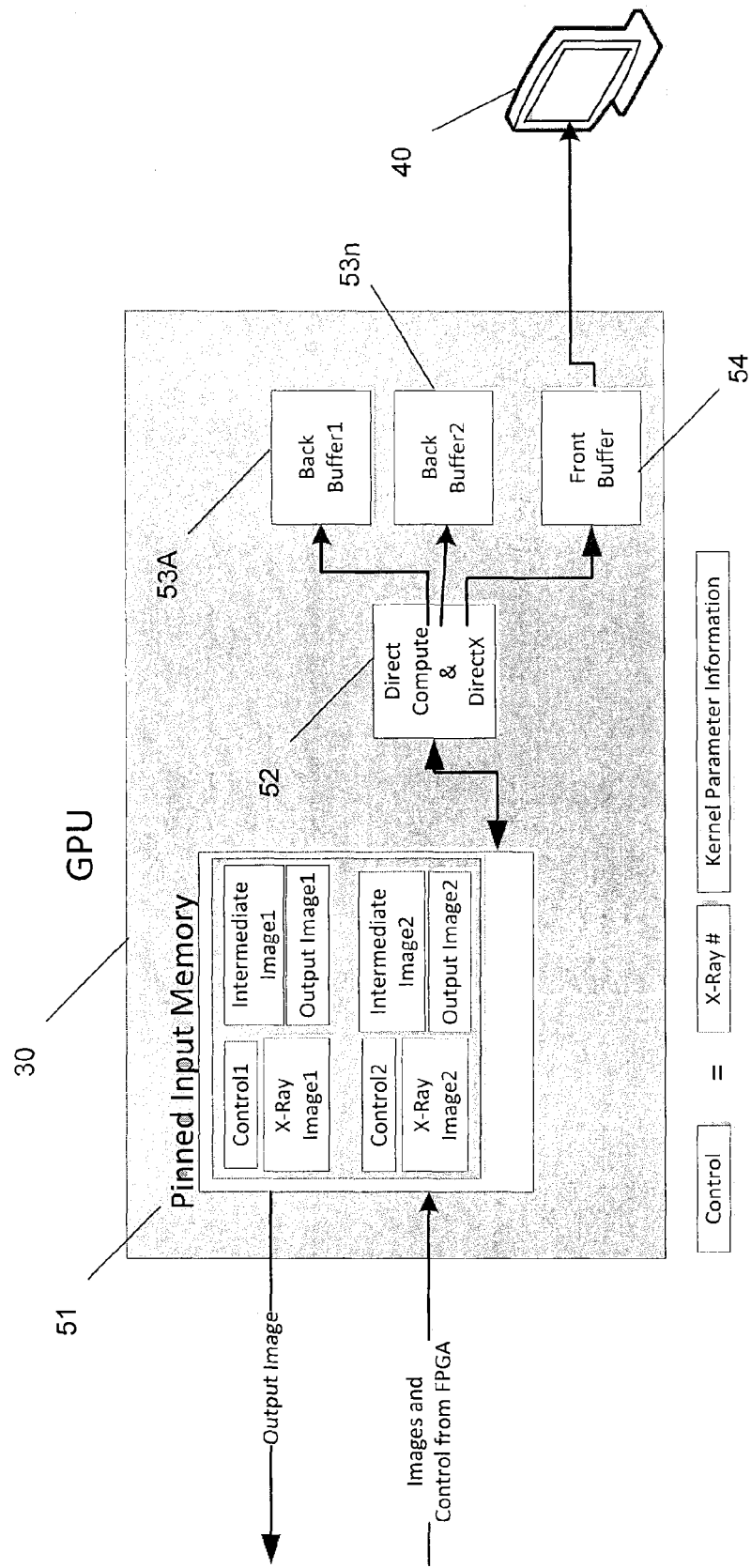
FIG. 3 is a schematic diagram illustrating the graphics processing unit according to one embodiment.

FIG. 3 illustrates the detailed functionality of the GPU 30. The GPU 30 includes pinned input memory 51, a kernel processing element 52, and back buffers 53-55. The pinned input memory 51 is bus (.i.e., PCIe bus) addressable memory within the GPU 30. The memory may be allocated by the GPU vendor's extension (e.g. AMD's). Instead of using such pinned memory, system memory that is (in one embodiment directly) accessed by the GPU 30 could also be used. FIG. 3 further illustrates the buffer information that is written into the GPU 30 from the real-time controller processing circuitry 10. In particular, in addition to generating images for display, the GPU 30 also implements processing on the image. The GPU 30 informs the real-time controller processing circuitry 10 when processing is complete and, in one embodiment, the real-time controller processing circuitry 10 is able to retrieve the processed image in response to this information.

As previously described, the real-time controller processing circuitry 10 is able to directly DMA image and control information into a buffer of the GPU 30 pinned memory 51. The GPU 30 pinned memory 51 is memory on the GPU board that is mapped to PCIe memory space. External devices are able to read and write to this memory using PCIe master capability. The larger the size of the buffer, the more decoupled the real-time controller processing circuitry 10 and the GPU 30 can become. However, since the system is real-time, the end-to-end latency of the system can be very low, thus, there is sometimes less benefit to using too large of a buffer.

In one embodiment, three buffers can be used in the pinned memory 51. In one embodiment, each buffer may consist of two different sub-buffers, e.g. an image buffer and a control buffer. The control buffer contains all parameter information needed by the kernels. The control buffer may be fixed and include parameter information for every kernel, even if the kernel is not being used to process the image. This configuration can reduce implementation, test, and debug time. The control buffer may also include an X-ray image number, which continues to be associated with the X-ray image throughout its processing. The image number is a monotonically increasing counter that is incremented with each new image and is reset with each new dataflow. The image number is not directly used by the GPU 30 except to keep track of processing in the GPU 30.

After the real-time controller processing circuitry 10 has finished writing the latest image and control buffer to the GPU 30, a buffer index can be stored in a head register in the pinned GPU memory 51. Since the size of this head register is sufficiently small, it is guaranteed that the read and writes to this location are atomic. In particular, atomic means that read and write to this register by one device (i.e., GPU 30 or real-time controller processing circuitry 10) could not be interrupted by the read/write of another device (i.e. GPU 30 or real-time controller processing circuitry 10). One read or write operation by one device is guaranteed to finish before another read or write operation by another device. This is very important since there is often no mutex lock (mutual exclusive lock) available. In this example, this header register could be written by the real-time controller processing circuitry 10 at any time, and could be read by GPU 30 at any time. If the size of the register is large, some kind of synchronization mechanism is needed to avoid race condition to make sure that a read value is not corrupted by a write operation. In many circumstances, there is no mutex lock implementation in GPU kernel (i.e., DirectX Shaders) that prevents a write by the real-time controller processing circuitry 10 while GPU 30 is performing a read.

The GPU 30 will use this value to determine what buffer to process in the GPU 30. The GPU 30 accomplishes this by storing a tail value in a memory that stores the buffer index that was most recently processed. If the head is different than the tail, the GPU 30 can increment the tail, perform a mod (modulo operator function) with the buffer length and then process the buffer associated with the updated tail index.

Since real-time controller processing circuitry 10 and GPU 30 communication is asynchronous, it is possible that the head index may not have changed since the last time the GPU 30 processed the buffers. In this case, the GPU 30 will just reprocess the same image. Multiple buffers are used so that the real-time controller processing circuitry 10 can write to the GPU 30 while the GPU 30 is reading from another buffer. It is also possible that the real-time controller processing circuitry 10 can update more than one buffer entry before the GPU 30 reads the head value. The GPU 30 is able to process all images in order.

To avoid overwriting of data that has yet to be processed by the GPU 30, the real-time controller processing circuitry 10 will not write to a buffer unless the real-time controller processing circuitry 10 knows there is an "empty" entry in the buffer. The term "empty" denotes that the GPU 30 has finished reading out the image. To accomplish this, the real-time controller processing circuitry 10 keeps a local counter that the real-time controller processing circuitry 10 uses to keep track of how many buffers are empty in the GPU buffer. This counter is initialized to the size of the buffer and acts as kind of credit mechanism. The counter is decremented each time the real-time controller processing circuitry 10 finishes writing a new image to the GPU 30. When the GPU 30 finishes processing an image, the GPU 30 will inform the real-time controller processing circuitry 10 by updating a register in the GPU pinned memory 51 that is polled by the real-time controller processing circuitry 10. The real-time controller processing circuitry 10 increments the counter when the real-time controller processing circuitry 10 detects that an image has completed processing. Since overwriting a buffer is protected against, the GPU 30 can process the control and data buffers in place. There is no need to immediately copy the buffers to non-pinned memory. To avoid read/write conflicts with the buffers, the real-time controller processing circuitry 10 writes buffer data before updating the head register.

The GPU 30 may include a pinned memory 51 that is connected to the kernel processing element 52, which is connected to at least one back buffer 53*a*-53*n* and at least one front buffer 54.

The back buffer 53*a*-53*n* is used in the GPU 30 to hold the final image results that should be displayed in future updates to the display.

The front buffer 54 is the GPU output buffer that is currently displayed on the display device 40.

The kernel processing element 52 is included in the GPU and is configured to execute the kernel using processing circuitry. The kernel is a GPU program that is written in a parallel language (e.g., OpenCl, CUDA, DirectCompute, etc.) and used to control the processing in the GPU 30. The kernel is normally compiled and loaded into the GPU 30, where it can then be invoked as required.

The pinned input memory 51 stores both images and control information from the real-time controller processing circuitry 10 and stores output images, which are transferred out of the GPU 30 when necessary.

Figure 4:
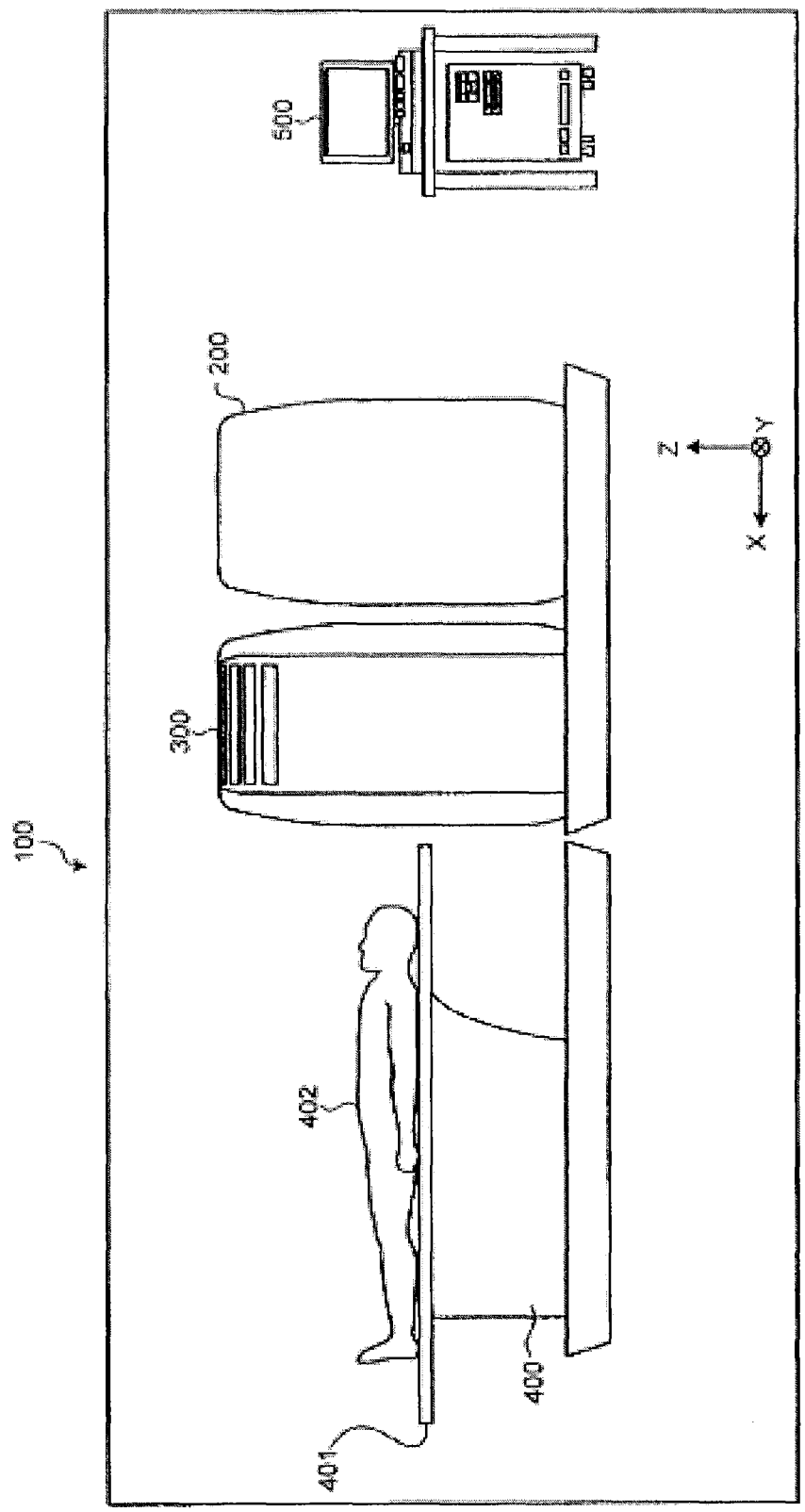
FIG. 4 is an explanatory diagram illustrating an example of a nuclear medicine imaging apparatus.

FIG. 4 is an explanatory diagram illustrating an example of a nuclear medicine imaging apparatus. As is shown in FIG. 4, an example of the nuclear medicine imaging apparatus as the PET system includes a PET-CT apparatus 100. In FIG. 4, 200 denotes a PET scanner, 300 denotes an X-ray CT scanner, 400 denotes a bed, 401 denotes a tabletop on which a subject is lying, and 402 denotes the subject. The PET-CT apparatus 100 includes the PET scanner 200, the X-ray CT scanner 300, the bed 400, and a console device 500. The X-direction in FIG. 4 represents a direction of the body axis of the subject 402 lying on the tabletop 401 illustrated in FIG. 4. The Y-direction represents a direction orthogonal to the X-direction on a horizontal plane. The Z-direction represents a vertical direction.

The bed 400 includes the tabletop 401 on which the subject 402 is lying. Furthermore, the bed 400 includes a bed control unit, implemented by circuitry which is not illustrated in FIG. 4, for moving the tabletop 401. The bed control unit is controlled by the console device 500 and moves the subject 402 lying on the tabletop 401 into an imaging bore of the PET-CT apparatus 100.

The PET scanner 200 includes a plurality of photon counting gamma ray detectors (to be described later) that count light derived from gamma rays for reconstructing a PET image. The gamma ray detectors are arranged in a ring shape around the body axis of the subject 402. The gamma ray detectors, from outside of the body of the subject 402 lying on the tabletop 401, detect a pair of gamma rays (pair annihilation gamma rays) emitted from the inside of the body of the subject 402, for example.

Specifically, every time the gamma ray detectors count the gamma rays, the PET scanner 200 collects counting information including the detection position indicating the position of a gamma ray detector that detects the gamma rays, the energy value at the time when the gamma rays are incident on the gamma ray detector, and the detection time at which the gamma ray detector detects the gamma rays. The detection time is collected. This causes the PET-CT apparatus 100 to reconstruct a PET image in which a path of the heavy particle beam is visualized.

The X-ray CT scanner 300 includes an X-ray tube that emits X-rays for reconstructing an X-ray CT image and an X-ray detector that detects the X-rays emitted by the X-ray tube. In the X-ray CT scanner 300, the X-ray tube irradiates the subject 402 with the X-rays, and the X-ray detector detects the X-rays passing through the subject 402. Specifically, the X-ray tube emits the X-rays, and the X-ray detector detects the X-rays while the X-ray CT scanner 300 is rotating about the body axis of the subject 402. In other words, the X-ray CT scanner 300 irradiates the subject with the X-rays in multi-directions, and detects the attenuated X-rays absorbed in the subject 402 by passing through the subject 402 while being rotating about the body axis of the subject 402. Data generated by performing amplification processing, A/D conversion processing, and the like on the X-rays detected by the X-ray detector is also referred to as "X-ray projection data". The X-ray CT scanner 300 collects the X-ray projection data and the detection position at which the X-rays used for generating the X-ray projection data are detected.

Figure 5:
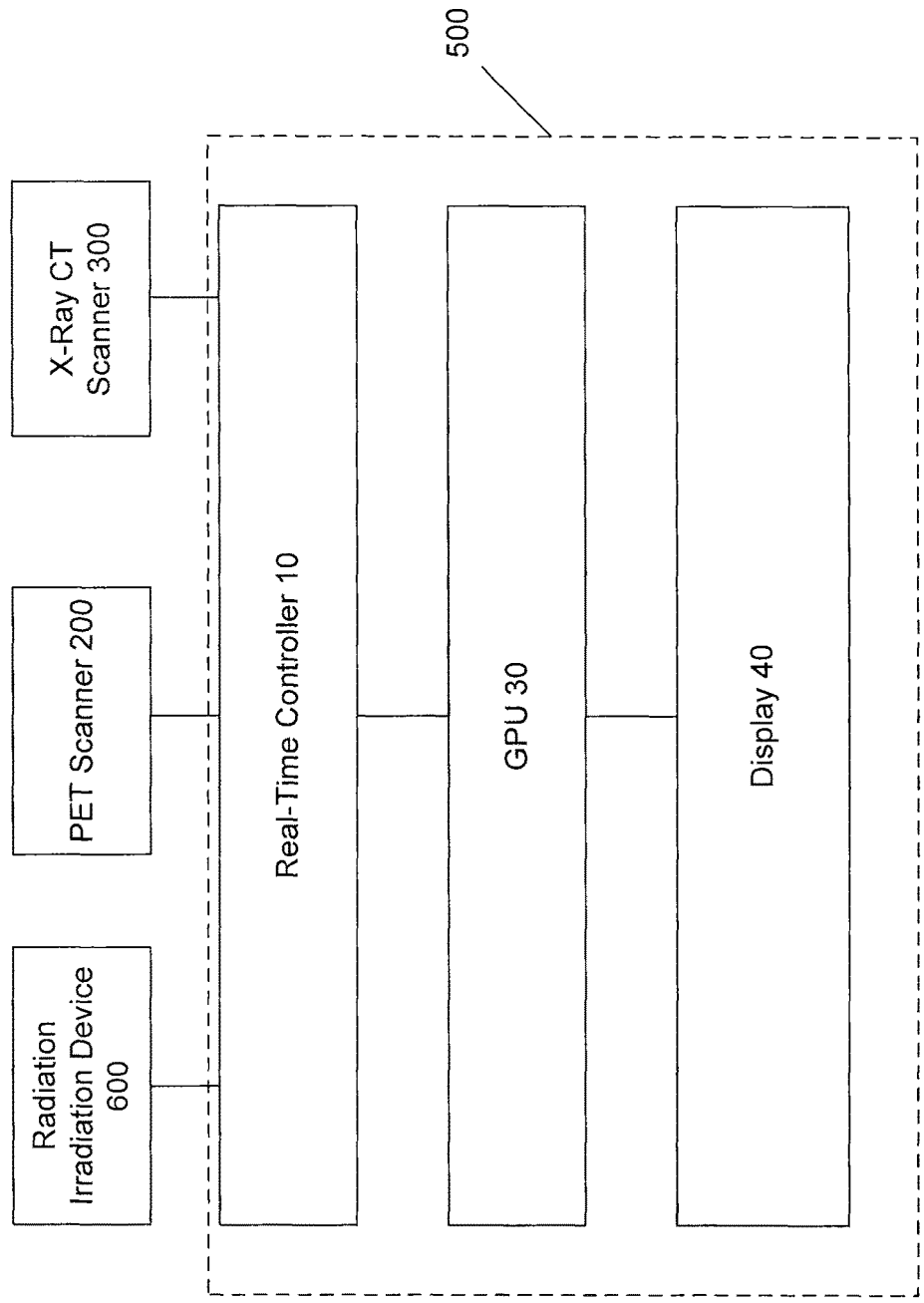
FIG. 5 is a block diagram of an exemplary configuration of the console device according to the embodiment.

FIG. 5 is a block diagram of an exemplary configuration of the console device according to the embodiment. The console device 500 reconstructs an X-ray CT image based on the information collected by the X-ray CT scanner 300. Furthermore, the console device 500 generates coincidence counting information by using the counting information collected by the PET scanner 200, and reconstructs a PET image based on the coincidence counting information thus generated. In the description below, the processing for reconstructing a PET image and the processing for reconstructing an X-ray CT image by the console device 500 may be performed by using an arbitrary method, and an explanation thereof will be made succinctly.

In the example illustrated in FIG. 5, the PET scanner 200, the X-ray CT scanner 300, and a radiation irradiation device 600 are illustrated in addition to the console device 500 as a matter of convenience for explanation. As shown in FIG. 5, the console device 500 includes a display 40, a real-time controller 10 and a GPU 30. The GPU 30 reconstructs an X-ray CT image as described above. Furthermore, the real-time controller 10 and the GPU 30 of the console device 500 are able to reconstruct a PET image. In the embodiment, an explanation is made of the case where one console device 500 reconstructs an X-ray CT image and a PET image. However, the embodiment can be applied to the case where reconstruction of an X-ray CT image and reconstruction of a PET image are performed in different console devices.

The real-time controller 10 controls the reconstruction processing of a PET image and the reconstruction processing of an X-ray CT image in the console device 500. Furthermore, the display 40 displays a PET image, an X-ray CT image, a superimposed image of a PET image and an X-ray CT image, or the like on the display.

The real-time controller 10 and GPU 30 is able to perform back projection processing on the X-ray projection data by the filtered back projection (FBP) method, for example, thereby reconstructing an X-ray CT image.

The real-time controller 10 and GPU 30 generates a combination of two pieces of counting information whose difference in detection time is within a time window among the counting information as coincidence counting information obtained by counting pair annihilation gamma rays nearly coincidentally.

Specifically, the coincidence counting information is generated based on conditions of coincidence counting information generation specified by an operator. The conditions of coincidence counting information generation include the time window, for example. The time window indicates an upper limit of difference between two detection times in the case where a pair of gamma rays are both counted.

For a pair of gamma rays emitted coincidentally from a positron-emitting radionuclide, the detection times of the gamma rays each included in the pair of gamma rays are the same, or difference between the two detection times is small even if the detection times are not the same. As a result, the time window is used to prevent false coincidence counting information from being generated.

For example, an explanation will be made of the case where the coincidence counting information is generated by using a time window of "10 nanoseconds". In this case, the "detection time (T)" of each module is referred to, and a combination of the counting information is searched for whose difference between two detection times is within a "time window of 10 nanoseconds" among the modules.

Searching for a combination in which the detection time is within the time window is also referred to as "coincidence finding". A list of the generated coincidence counting information is also referred to as a "coincidence list".

An energy window may be set as the conditions of coincidence counting information generation. The energy value of a pair of gamma rays emitted by annihilation of a positron is already specified in advance. For example, elements each emit gamma rays of "511 keV". Therefore, any gamma rays emitted coincidentally from a positron-emitting radionuclide have an energy value within a predetermined range. As a result, the energy window is used to exclude counting information not of the pair of gamma rays emitted from the positron-emitting radionuclide, and the coincidence counting information is generated. Thus, false coincidence counting information can be prevented from being generated. As described above, setting the conditions of coincidence counting information generation makes it possible to perform random correction for excluding accidental coincidence counting, scatter correction for preventing counting information of scattered gamma rays from being generated as the coincidence counting information, sensitivity correction for correcting difference in sensitivity among the detectors, and other correction.

The generated coincidence counting information is used to reconstruct a PET image. Specifically, the coincidence counting information is considered to be projection data of the gamma rays, and the PET image is reconstructed from the projection data of the gamma rays by using a successive approximation method. The successive approximation methods include a maximum likelihood expectation maximization (MLEM) method, and an ordered subset MLEM (OSEM) method in which the convergence time is significantly shortened by improving the algorithm of the MLEM method.

Figure 6:
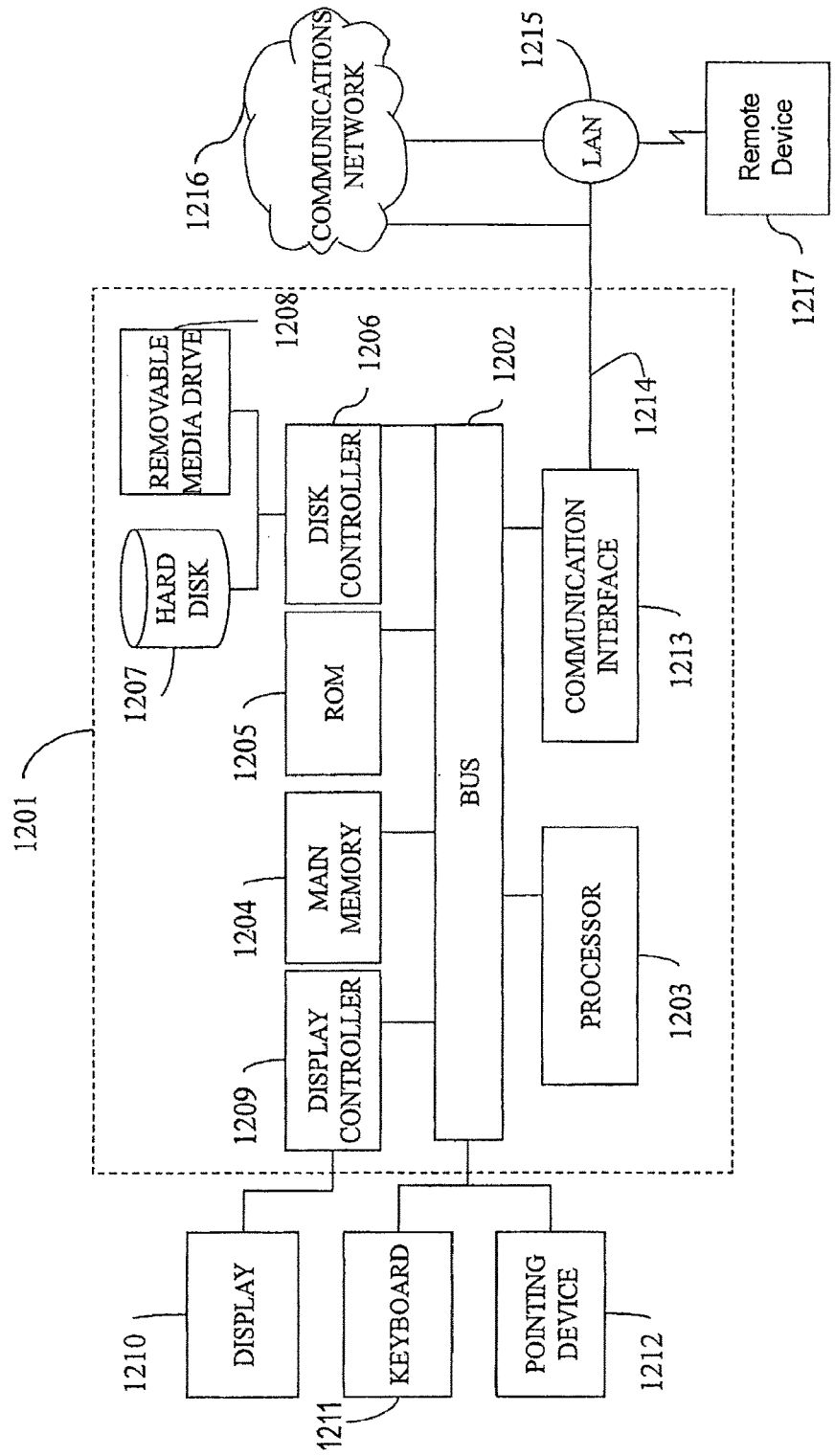
FIG. 6 is a schematic diagram illustrating a computing system according to an embodiment.

FIG. 6 illustrates a computer system 1201 upon which embodiments of the present disclosure may be implemented. For example, the CPU 20 can be implemented as computer system 1201. The computer system 1201 may include the various above-discussed components with reference the above figures, which perform the above-described process.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 such as a GPU (or display adapter) coupled to the bus 1202 to control a display 1210 (or display) such as a liquid crystal display (LCD), for displaying information to a computer user. The computer system includes input devices, such as a keyboard 1211 and a pointing device 1212, for interacting with a computer user and providing information to the processor 1203 (or processing device/unit) such as the CPU. The pointing device 1212, for example, may be a mouse, a trackball, a finger for a touch screen sensor, or a pointing stick for communicating direction information and command selections to the processor 1203 and for controlling cursor movement on the display 1210.

The computer system 1201 performs a portion or all of the processing steps of the present disclosure in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a remote device 1217 such as a personal digital assistant (PDA), mobile device, server, desktop or laptop computer, or cellular telephone. Data may be transmitted to a remote device from the real time controller, the GPU or the CPU.

The present embodiments provide significant advantages. For example, the system permits real-time display and processing on the same system. Further, off-the-shelf graphics cards can be utilized for portions of the system. The graphics card (e.g., GPU 30) can also perform image processing, leaving the real-time controller processing circuitry 10 to perform other tasks instead of the image processing. The processed images can be sent back to the real-time controller processing circuitry 10. The system can also support multiple GPUs and each GPU can support multiple data flows. When multiple GPU's are used, either 1) there is no communications between GPUs, all GPUs communicate directly with the real-time controller processing circuitry(s), or 2) some or all GPUs could communicate with each other, and some or all of the real-time controller processing circuitry(s), the topology could really vary (also depending on the communication mechanism available between GPUs).

Because no synchronization is required between the CPU 20, the real-time controller processing circuitry 10, and the GPU 30, low-level control information and images can be sent by the the real-time controller processing circuitry 10 directly to the GPU 30. The GPU 30 then decides what input data should be processed and with what parameters. The CPU 20 only decides what kernel processes to run on an image and when to display the result, thereby limiting the CPU 20 to high-level control. As a result, the GPU 30 can run at full performance even when the operating system of the CPU 20 is temporarily unavailable.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

It is noted that, as used in the specification, the singular forms "a," "an," and "the" may also include plural referents unless the context clearly dictates otherwise.

The invention claimed is:

1. An asynchronous medical image processing system, comprising:
a real-time controller connectable to a medical imaging device;
a graphics processing unit (GPU) connectable to a display device; and
a central processing unit (CPU) configured to execute an operating system and related application(s),
wherein the real-time controller is directly connected to a memory of the GPU and performs respective operations asynchronously with respect to the CPU,
wherein the real time controller is configured to obtain medical imaging data, generate first instructions for the medical imaging-data and transmit the medical imaging data and the first instructions to the memory of the GPU,
wherein the GPU is configured to receive and process the medical imaging data based on the first instructions from the real-time controller and second instructions sent independently from the CPU, wherein the second instructions are instructions corresponding to a higher level of control than the first instructions, and
wherein the CPU is configured to generate the second instructions for display of multiple future image frames and transmit the second instructions to the GPU.

2. The asynchronous medical image processing system according to claim 1, wherein the real-time controller is connected to the CPU.

3. The asynchronous medical image processing system according to claim 2, wherein the real-time controller informs the CPU that processing has started before or when transferring the medical imaging data to the GPU.

4. The asynchronous medical image processing system according to claim 1, wherein GPU is configured to transfer a processed image to the real-time controller generated from the medical imaging data once the medical imaging data is processed.

5. The asynchronous medical image processing system according to claim 1, wherein the real-time controller is connected to the CPU via an application programming interface.

6. The asynchronous medical image processing system according to claim 1, wherein the real-time controller is connected to a pinned memory of the GPU.

7. The asynchronous medical image processing system according to claim 1, wherein the GPU outputs images for display via a back buffer.

8. A real-time controller connectable to a medical imaging device, comprising:
processing circuitry configured to
obtain medical imaging data,
generate first instructions for the medical imaging data, and
transmit the medical imaging data and the first instructions to a memory of a graphic processing unit (GPU) connectable to a display device,
wherein the real-time controller is directly connected to a memory of the GPU and performs respective operations asynchronously with respect to a central processing unit configured to execute an operating system and related application(s),
wherein the processing circuitry is further configured to generate second instructions for display of multiple future image frames and transmit the second instructions to the GPU, and
wherein the second instructions are instructions corresponding to a higher level of control than the first instructions.

9. The real-time controller according to claim 8, wherein the real-time controller is connected to a CPU configured to execute an operating system and related application(s).

10. The real-time controller according to claim 9, wherein the real-time controller informs the CPU that processing has started before or when transferring the medical imaging data to the GPU.

11. The real-time controller according to claim 9, wherein the real-time controller is connected to the CPU via an application programming interface.

12. The real-time controller according to claim 8, wherein GPU is configured to transfer a processed image to the real-time controller generated from the medical imaging data once the medical imaging data is processed.

13. The real-time controller according to claim 8, wherein the real-time controller is connected to a pinned memory of the GPU.

14. The real-time controller according to claim 8, wherein the GPU outputs images for display via a back buffer.

15. A method for asynchronously processing medical images, using a medical image processing apparatus including a real-time controller connectable to a medical imaging device, a graphics processing unit (GPU) connectable to a display device, and a central processing unit (CPU) configured to execute an operating system and related application(s), the real-time controller being directly connected to a memory of the GPU and performing respective operations asynchronously with respect to the CPU, comprising:

obtaining, at the real time controller, medical imaging data, generating, at the real time controller, first instructions for the medical imaging-data;

transmitting, from the real time controller, the medical imaging data and the first instructions to the memory of the GPU;

receiving the medical imaging data at the GPU; and processing, at the GPU, the medical imaging data based on the first instructions from the real-time controller and second instructions sent independently from the CPU, wherein the second instructions are instructions corresponding to a higher level of control than the first instructions.

16. The method according to claim 15, further comprising:

informing, from the real-time controller, the CPU that processing has started before or when transferring the medical imaging data to the GPU.

17. The method according to claim 15, further comprising:

transferring, from the GPU, a processed image to the real-time controller generated from the medical imaging data once the medical imaging data is processed.

18. The method according to claim 15, further comprising:

outputting, from the GPU, images for display via a back buffer.

* * * * *